Aug. 4, 1964 M. W. STAPLES Plant Pat. 2,431

RED MAPLE

Filed June 19, 1963

INVENTOR.

MILFRED W. STAPLES

BY

Oberlin, Maky & Donnelly

ATTORNEYS

United States Patent Office

Plant Pat. 2,431
Patented Aug. 4, 1964

2,431
RED MAPLE

Milfred W. Staples, 416 E. Summit St., Kent, Ohio

Filed June 19, 1963, Ser. No. 289,149
1 Claim. (Cl. Plt.—51)

Figure 1:
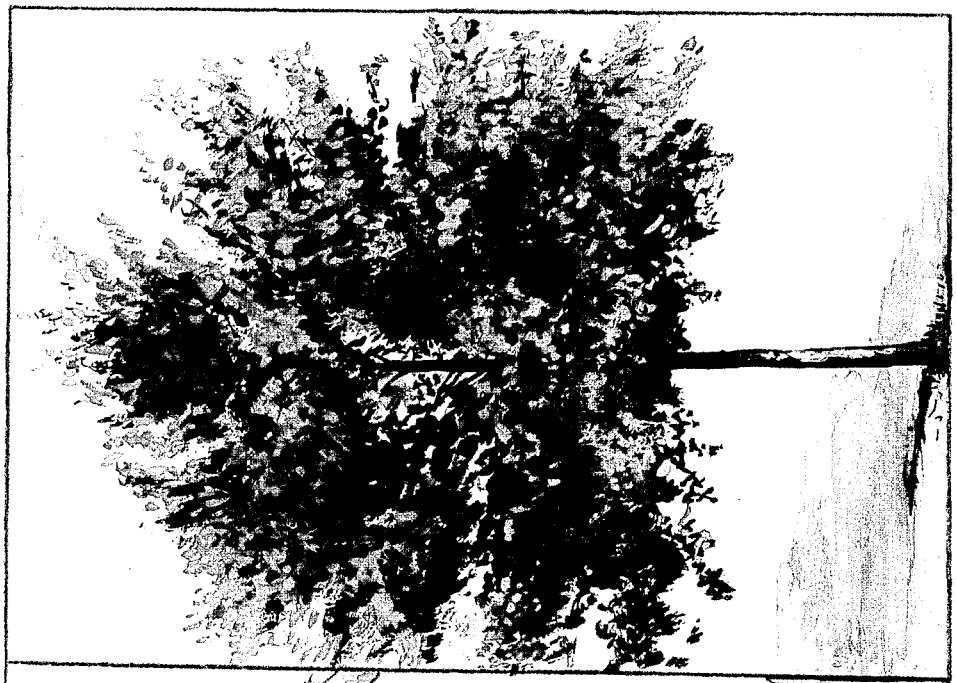

The present invention relates to a new and distinct clon of red maple tree, *Acer rubrum* L., discovered by me, having novel autumn coloring characteristics as will be hereinafter more particularly pointed out.

I have propagated my new red maple tree at Portland, Oregon, and in Ohio, asexually by budding, and the tree can be very readily propagated in this manner, perpetuating all of its original character. The original parent specimen was a tree discovered by me in Kent, Ohio, and has been under observation and study for eight years. The tree is now approximately 30 feet high with a crown spread of 24 feet and a trunk diameter of 10 inches four feet above the ground. The rate of growth appears to be somewhat slower than ordinary with the species. The clon is upright spreading in its growth habit, with symmetrically arranged branches well spaced and diverging at an angle in a manner to impart strength to the crotches. The oval crown is well proportioned to the trunk which has good basal development with no indication of girdling roots. The bark of the twigs is red and that of the larger branches and trunk is gray, being typical of the species. The leaves are predominantly three-lobed with the margins of the triangular lobes crenate-senate. The leaves are palmately veined, medium green, somewhat glossy above, glaucous below, and slightly hairy on the veins. They are 5–10 cm. in length, 4–8 cm. in width, and broadly crenate to slightly sub-cordate at the base. The petioles are red, 4–10 cm. in length, and the flowers and fruits are typical of the species. In general, while this clon is a good specimen of the species and accordingly evidences the desirable attributes thereof, it is generally typical except for the autumn coloring characteristics of the foliage.

The outstanding characteristics of this clon and the major differences between it and the species are the exceptional fall coloring of the foliage and its ability to transmit its unique autumn coloration to its asexually propagated progeny.

Figure 2:
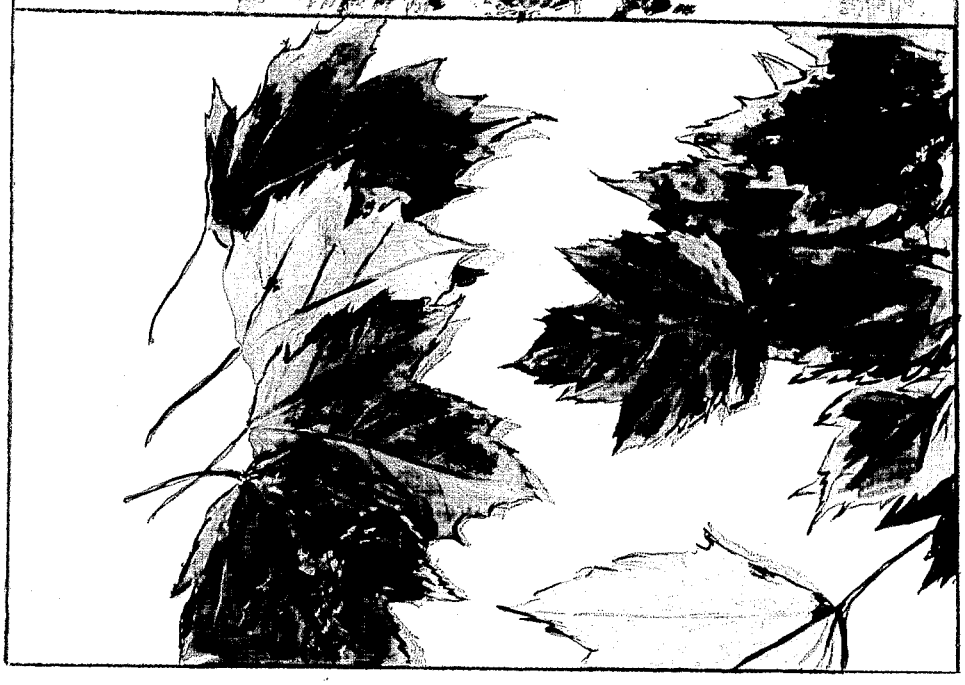

Referring to the drawing:

FIG. 1 shows the red maple of this invention at an age of approximately 29 years in the fall of the year; and FIG. 2 is a detail view of certain leaves taken therefrom exhibiting typical autumn color.

While the tones and shades of coloring of the leaves in autumn are, of course, variable through a fairly wide spectrum, the larger proportion of the foliage in autumn ranges from Marigold Orange (11/2) to Cardinal Red (822) on the "Horticultural Colour Chart," published by the British Colour Council in collaboration with The Royal Horticultural Society (Great Britain, Henry Stone & Son, Ltd.), or mottled red and green, and regularly repeats such performances every autumn. Moreover, this characteristic is reliably passed on to the tree's asexually reproduced progeny. In consequence, this clon is unusually desirable as a lawn specimen or as a street tree and may be asexually reproduced and sold by nurserymen with the assurance that the desired characteristics will be evidenced by the progeny they distribute and sell.

I claim:

A new and distinct variety of red maple, *Acer rubrum* L., of upright spreading symmetrical growth habit characterized by the unusual foliage coloration described above, and by the ability to transmit such characteristics to all or substantially all of its asexually reproduced progeny.

No references cited.